United States Patent
Luo et al.

(10) Patent No.: US 10,113,963 B1
(45) Date of Patent: Oct. 30, 2018

(54) INTEGRATED SYSTEMS AND PROCESSES FOR ONLINE MONITORING OF A CHEMICAL CONCENTRATION IN A FLOW OF A DEGASSED IONIC LIQUID

(71) Applicant: Chevron U.S.A. Inc., San Ramon, CA (US)

(72) Inventors: Huping Luo, El Cerrito, CA (US); Hye-Kyung Cho Timken, Albany, CA (US); Toni Zhang Miao, Orinda, CA (US); Howard Steven Lacheen, Richmond, CA (US); Bi-Zeng Zhan, Albany, CA (US)

(73) Assignee: Chevron U.S.A. Inc., San Ramon, CA (US)

( * ) Notice: Subject to any disclaimer, the term of this patent is extended or adjusted under 35 U.S.C. 154(b) by 0 days.

(21) Appl. No.: 16/018,143

(22) Filed: Jun. 26, 2018

Related U.S. Application Data

(63) Continuation of application No. 15/612,648, filed on Jun. 2, 2017.

(51) Int. Cl.
*G01J 3/00* (2006.01)
*G01N 21/552* (2014.01)
(Continued)

(52) U.S. Cl.
CPC .............. *G01N 21/552* (2013.01); *G01N 1/34* (2013.01); *G01N 21/15* (2013.01); *G01N 21/3577* (2013.01); *G01N 2021/3595* (2013.01)

(58) Field of Classification Search
CPC .. G01N 21/314; G01N 21/33; G01N 21/3504; G01J 3/10; G01J 3/42
(Continued)

(56) References Cited

U.S. PATENT DOCUMENTS 7,285,698 B2   10/2007   Liu et al.
7,432,408 B2   10/2008   Timken et al.
(Continued)

FOREIGN PATENT DOCUMENTS

WO   2014005985 A1   1/2014
WO   2016202905 A1   12/2016

OTHER PUBLICATIONS

FT-IR Spectroscopy inside a Glovebox, www.brukeroptics.com.
(Continued)

*Primary Examiner* — Md M Rahman
(74) *Attorney, Agent, or Firm* — Susan M. Abernathy

(57) ABSTRACT

An integrated system for monitoring a chemical concentration in an ionic liquid, comprising:
a. an online FTIR instrument with an ATR window;
b. a sample conditioning station that removes light hydrocarbons and produces a degassed ionic liquid that is analyzed by FTIR; and
c. a solvent flushing system that flows solvent across the ATR window. Also, a process for monitoring the chemical concentration, comprising:
a. degassing the ionic liquid in the sample conditioning station;
b. passing the degassed ionic liquid over an ATR window;
c. periodically redirecting a flow of the degassed ionic liquid via a bypass line or an on-off valve that isolates the ATR window from the process unit that elutes the ionic liquid; and
d. flowing a solvent and a purging gas over the ATR window during the periodically redirecting step c); and
e. resuming the passing of the degassed ionic liquid over the ATR window.

20 Claims, 8 Drawing Sheets

(51) Int. Cl.
    *G01N 21/3577* (2014.01)
    *G01N 1/34* (2006.01)
    *G01N 21/15* (2006.01)
    *G01N 21/35* (2014.01)

(58) Field of Classification Search
    USPC .......................................................... 356/51
    See application file for complete search history.

(56) References Cited

U.S. PATENT DOCUMENTS

| | | |
|---|---|---|
| 7,432,409 B2 | 10/2008 | Elomari et al. |
| 7,495,144 B2 | 2/2009 | Elomari |
| 7,531,707 B2 | 5/2009 | Harris et al. |
| 7,886,577 B2 | 2/2011 | Zeng |
| 7,923,593 B2 | 4/2011 | Hommeltoft et al. |
| 8,362,095 B2 | 1/2013 | Schwab et al. |
| 8,375,768 B2 | 2/2013 | Zeng |
| 9,238,193 B2 | 1/2016 | Ji et al. |
| 9,782,744 B2 | 10/2017 | Warner |
| 2012/0245737 A1 | 9/2012 | Liu et al. |
| 2012/0296145 A1 | 11/2012 | Lacheen |
| 2015/0133711 A1 | 5/2015 | Ji et al. |
| 2016/0096784 A1 | 4/2016 | Ji et al. |
| 2016/0231267 A1 | 8/2016 | Swager et al. |

OTHER PUBLICATIONS

Visak et al, Solutions of ionic liquids with diverse aliphatic and aromatic solutes—Phase behavior and potentials for applications: A review article, Arabian Journal of Chemistry, Oct. 13, 2014.
Declaration.

INTEGRATED SYSTEMS AND PROCESSES FOR ONLINE MONITORING OF A CHEMICAL CONCENTRATION IN A FLOW OF A DEGASSED IONIC LIQUID

This application is a continuation of U.S. patent application Ser. No. 15/612,648, filed on Jun. 2, 2017, in Art Unit 2886; herein incorporated in its entirety.

TECHNICAL FIELD

This application is directed to integrated systems and processes for monitoring chemical concentrations in an ionic liquid using an online FTIR instrument.

BACKGROUND

Improved processes and systems are needed for continuously and reliably measuring and controlling a chemical concentration in ionic liquids.

SUMMARY

This application provides an integrated system for monitoring a chemical concentration in an ionic liquid, comprising:
a. an online FTIR instrument with an ATR window having a flow of a degassed ionic liquid to the ATR window;
b. a sample conditioning station comprising a flash drum, placed upstream from the ATR window, that removes light hydrocarbons from the ionic liquid and produces the degassed ionic liquid that is analyzed by the online FTIR instrument; and
c. a solvent flushing system that intermittently flows a solvent and a purging gas across the ATR window during periods when the flow of the degassed ionic liquid is not passed over the ATR window.

This application also provides a process for monitoring a chemical concentration in an ionic liquid, comprising:
a. degassing the ionic liquid in a sample conditioning station comprising a flash drum that is fluidly connected to a process unit utilizing the ionic liquid, wherein the sample conditioning station removes light hydrocarbons from the ionic liquid and produces a degassed ionic liquid;
b. passing the degassed ionic liquid in a flow over an ATR window of an online FTIR instrument;
c. periodically redirecting the flow of the degassed ionic liquid away from the ATR window via a bypass line or an on-off valve that isolates the ATR window from the process unit that elutes the ionic liquid; and
d. flowing a solvent and a purging gas over the ATR window during the periodically redirecting step c); and
e. resuming the passing of the degassed ionic liquid over the ATR window.

GLOSSARY

Figure 1:
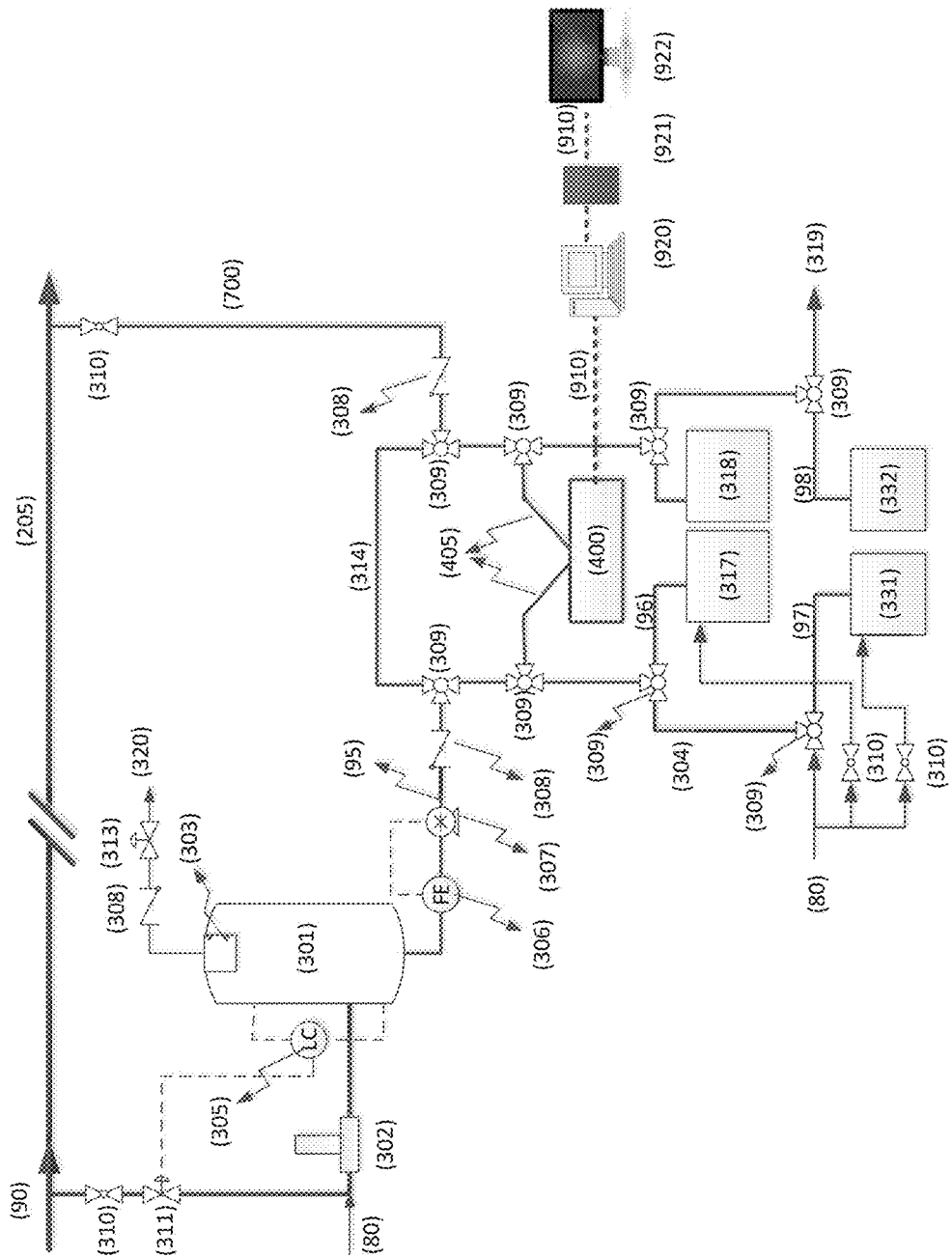
FIG. 1 is a diagram of an embodiment of the integrated system of this disclosure having a flow-through FTIR cell in the online FTIR instrument, a bypass line, and a sample conditioning station.

"Ionic Liquid" refers to a material consisting entirely of ions that is liquid below 100° C.

"Acidic ionic liquid" refers to a material consisting entirely of ions, that can donate a proton or accept an electron pair in reactions, and that is liquid below 100° C.

"Online", in the context of this disclosure, refers to a piece of equipment that is an essential part of an integrated system using an ionic liquid. "Online" may otherwise be referred to as 'in situ'.

"Periodic Table" refers to the version of the IUPAC Periodic Table of the Elements dated Jun. 22, 2007, and the numbering scheme for the Periodic Table Groups is as described in Chemical And Engineering News, 63(5), 27 (1985).

A "vent" refers to an outlet from the integrated system, and can be one or more of a duct, a flue, a shaft, a passage, or an airway.

"Attenuated total reflectance" (ATR) is a sampling technique used in conjunction with infrared spectroscopy which enables samples to be examined directly in the solid or liquid state without further preparation.

A "converter" receives measurements from a hazardous area instrument i.e., temperature sensors, potentiometers, spectrophotometers, or load cells, and converts and conditions the measurements into signals, such as 0/4 to 20 mA or 0/2 to 10V.

A "distributed control system" (DCS) is a computerized control system for a process or plant, in which autonomous controllers are distributed throughout the system, but there is central operator supervisory control.

DETAILED DESCRIPTION

Ionic liquids are known for complexing with and capturing chemicals. The integrated systems disclosed herein monitor the chemical concentration in the ionic liquid by the online Fourier Transform Infrared (FTIR) instrument with an ATR window. The integrated system provides quick and accurate measurements of the chemical concentration in the ionic liquid and can be very useful for understanding the operation of a process unit where the ionic liquid is being employed.

FTIR instruments with ATR windows provide for infrared radiation passing through the ATR window. The ATR window is a crystal with a high refractive index, allowing the infrared radiation to reflect with the ATR window either once or multiple times. The infrared radiation from a FTIR spectrometer enters the ATR window, onto which the ionic liquid is intimately contacted with a top surface of the ATR window. By intimately contacted is meant that the distance between the ionic liquid and the top surface of the ATR window is from 0 to 5 microns. The infrared radiation reflects through the ATR window into the ionic liquid, where it interacts with the chemicals in the ionic liquid. The backscattered infrared radiation is directed out of the ATR window and back into the normal beam path of the FTIR spectrometer.

Sample Conditioning Station 300:

The sample conditioning station 300, placed upstream from the ATR window, removes light hydrocarbons from the ionic liquid and produces a degassed ionic liquid 95 that is analyzed by the online FTIR instrument 400. The sample conditioning station 300 can remove the light hydrocarbons that interfere with the measurement of the chemical concentration being monitored. In one embodiment, for example, the sample conditioning station 300 can remove isobutane from an acidic ionic liquid in which the chemical concentration being monitored is a conjunct polymer. In another embodiment, the sample conditioning station 300 can remove uncaptured gaseous components in a process that uses an ionic liquid solvent to capture and recover gaseous components.

Figure 2:
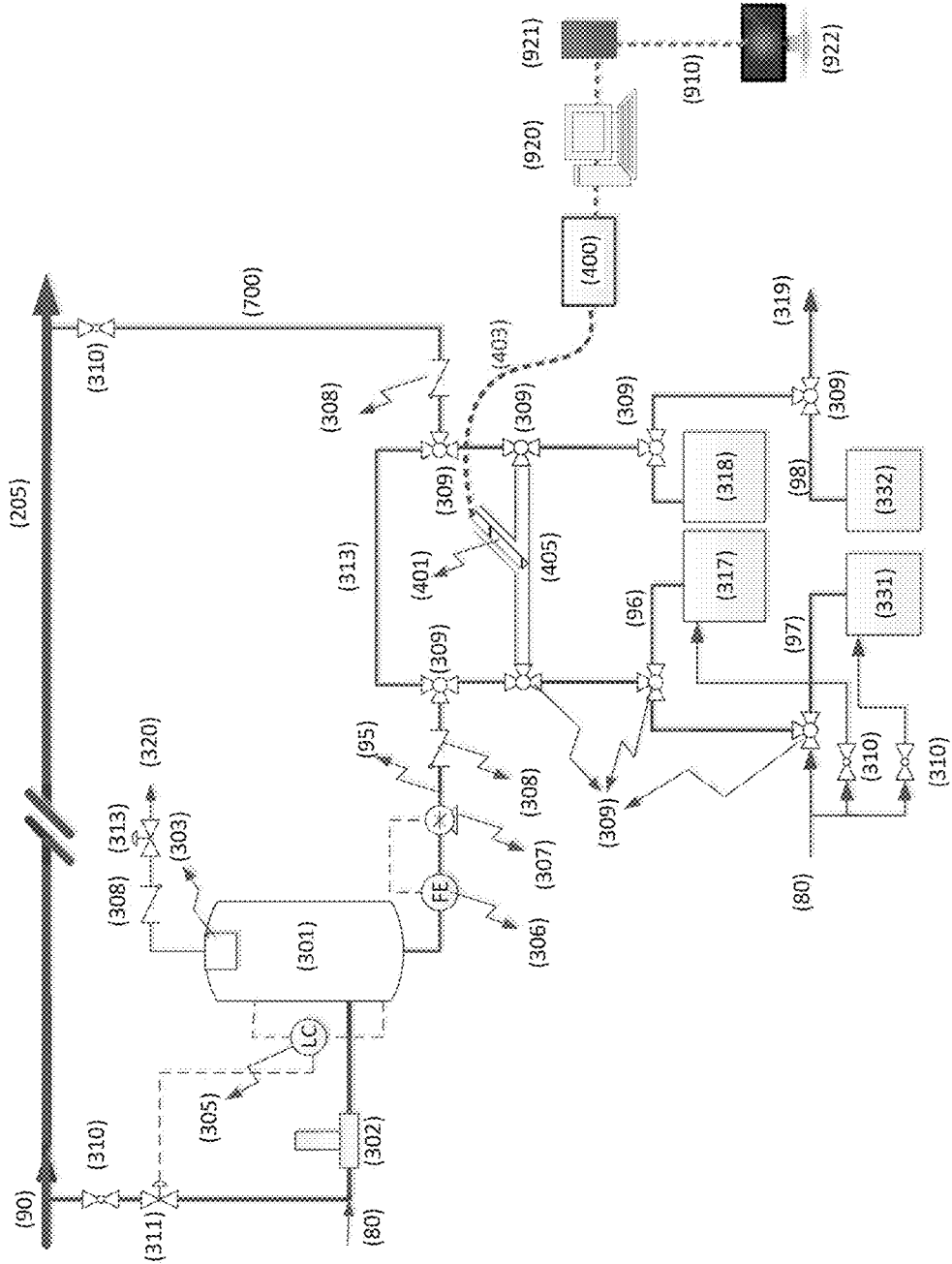
FIG. 2 is a diagram of an embodiment of the integrated system of this disclosure having an online FTIR instrument with a FTIR probe, a bypass line, and a sample conditioning station.
Figure 3:
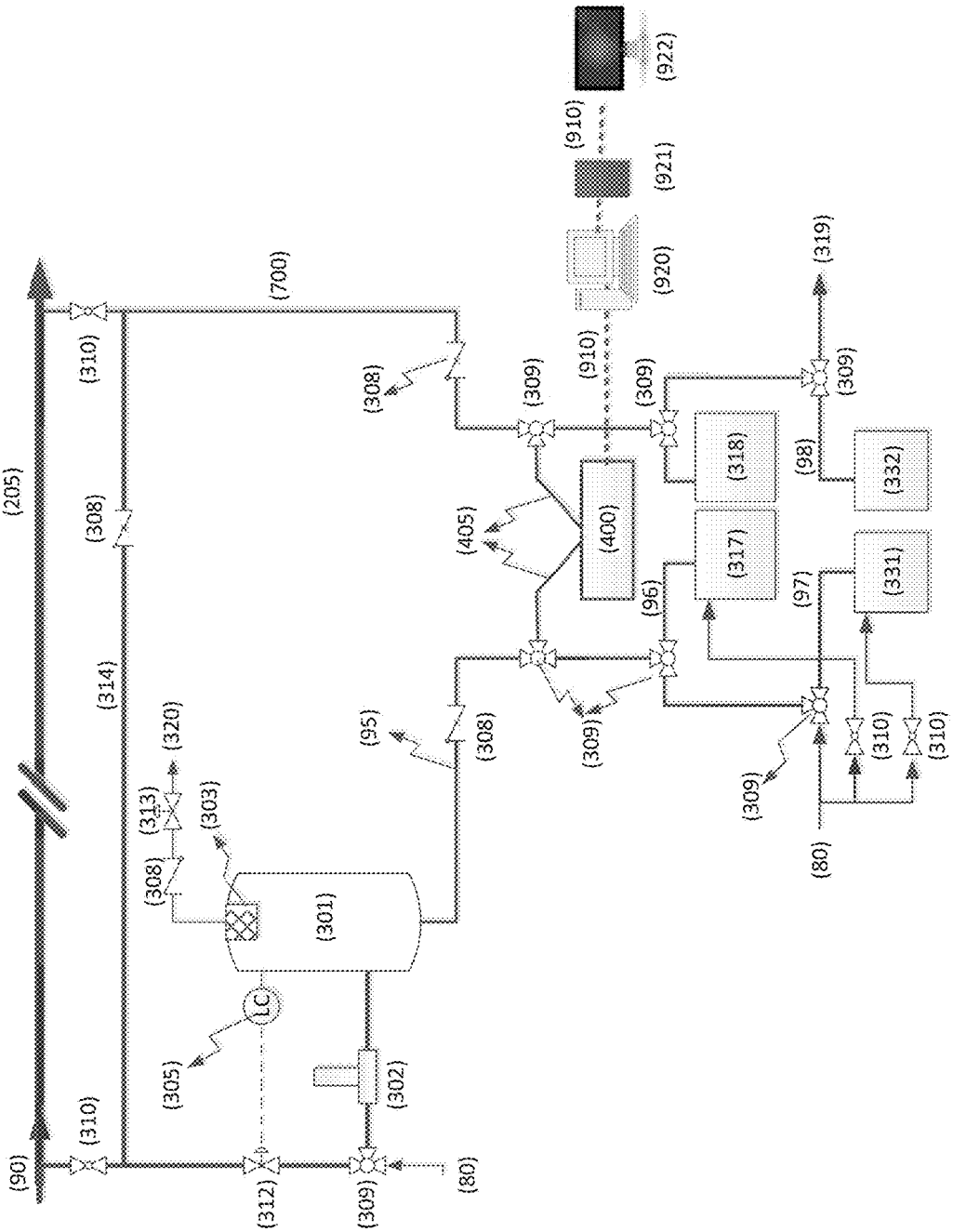
FIG. 3 is a diagram of an embodiment of the integrated system of this disclosure having an online FTIR instrument, an on-off valve, and a sample conditioning station.

Examples of sample conditioning stations 300 are shown in FIGS. 1-3. These sample conditioning stations 300 comprise a flash drum 301 with a level controller 305. A level control valve 311 can be used with the level controller 305, and the level control valve 311 can be placed far enough upstream from the flash drum 301 to give sufficient time for the light hydrocarbons in the ionic liquid to vaporize, and optionally to allow foam to collapse in the ionic liquid, if there is any. The flash drum 301 can provide a residence time for the ionic liquid that is effective for ensuring separation of the light hydrocarbons from the ionic liquid. In one embodiment, the residence time in the flash drum 301 is from 1 to 30 minutes. The level controller 305 can control the level of the ionic liquid in the flash drum 301 to provide the degree of separation of the light hydrocarbons from the ionic liquid. The level can be adjusted from 10 to 90 vol % of the flash drum.

The sample conditioning station 300 can also comprise a filter 302. This feature is shown in FIGS. 1-3. In these embodiments, the filter 302 is located upstream of the flash drum 301. The filter 302 can be placed in the sample conditioning station 300 to reduce a foam in the ionic liquid. The filter media used in the filter 302 can include any material that is compatible with the ionic liquid, with the light hydrocarbons in the ionic liquid, and with the chemical that is concentrated in the ionic liquid. The filter media should have a pore size that gives the degree of de-foaming that is needed, such as from 1 to 100 microns, from 5 to 50 microns, or from 10 to 20 microns. In FIGS. 1-3 the process for monitoring the chemical concentration in the ionic liquid additionally comprises de-foaming the ionic liquid with the filter 302 in the sample conditioning station 300 prior to the degassing of the ionic liquid in the sample conditioning station 300. In one embodiment, the filter 302 in the sample conditioning station 300 removes particulates in the ionic liquid that could foul the ATR window in the online FTIR instrument 400. In one embodiment, the filter 302 performs both de-foaming of the ionic liquid and removing of particulates from the ionic liquid.

In one embodiment, the process for monitoring the chemical concentration in a used ionic liquid 90 additionally comprises de-foaming the ionic liquid in the sample conditioning station 300 prior to the degassing. In one embodiment, the process comprises filtering the ionic liquid in the sample conditioning station 300 to de-foam and remove particulates from the ionic liquid. In one embodiment, the sample conditioning station 300 comprises a filter 302 that reduces a foam in the ionic liquid and removes particulates from the ionic liquid.

The sample conditioning station 300 can also comprise a demister 303 at the top of the flash drum 301 that keeps the ionic liquid in the flash drum 301 and provides better separation of the volatile light hydrocarbons from the ionic liquid. Examples of demisters 303 are mesh pads, vane packs, axial-flow cyclones, and filter coalescers.

A purging gas 80 can be used to purge the flash drum 301 of the light hydrocarbons and facilitate their removal from the top of the flash drum 301. Examples of purging gases are those that are inert to the processes being performed in the integrated system, that don't interfere with the measurements made by the online FTIR instrument 400, and that don't subsequently adversely contaminate the ionic liquid after passing through the integrated system. Examples of purging gasses 80 are inert gases that don't interfere with an activity of the ionic liquid or a measurement of the chemical concentration in the ionic liquid, such as nitrogen, helium, neon, argon, hydrogen, and mixtures thereof.

In one embodiment, an effluent comprising the light hydrocarbons exits from the flash drum 301 and is passed to a scrubber 320. A scrubber 320 is a pollution control device that uses liquid to wash unwanted pollutants from the light hydrocarbons in the eluted gas stream.

Solvent Flushing System 330:

The solvent flushing system 330 is used to periodically clean the ATR window and ensure that intimate contact between the ATR window and the ionic liquid is achieved and maintained. The solvent flushing system 330 is operated to intermittently flow a solvent 97 and a purging gas 80 across the ATR window during periods when a flow of the degassed ionic liquid 95 is not passed over the ATR window. The solvent flushing system 330 can also be used to dissolve and remove any particulates or other contaminants that can collect on the ATR window surface and interfere with the accuracy of the measurement of the chemical concentration. In one embodiment, the process for monitoring the chemical concentration in the ionic liquid includes flowing the solvent 97 over the ATR window during the periodically directing step, wherein a hydrolyzed ionic liquid, a corrosion product, or a mixture thereof, that had adhered to the ATR window, is dissolved and removed by the solvent 97.

As shown in FIGS. 1-3, the solvent flushing system 330 can comprise a fresh solvent reservoir 331 from which the solvent 97 is fed to the ATR window. The solvent flushing systems 330 shown in these figures can also comprise a used solvent reservoir 332 that collects a used solvent after the solvent 97 has passed over the ATR window. In one embodiment, the solvent flushing system 330 comprises a fresh solvent reservoir 331 that is connected to a source of the purging gas 80 and the purging gas 80 directs a solvent flow from the fresh solvent reservoir 331 through the online FTIR instrument 400 or across the ATR window in a FTIR probe 401.

The solvent 97 is selected based on the ionic liquid and the chemical that is being monitored. In one embodiment, the solvent 97 should be one that solubilizes the ionic liquid, solubilizes the chemicals captured or solubilized in the ionic liquid, and solubilizes any materials that may have collected on the ATR window. In one embodiment, the solvent 97 is polar. The miscibility of ionic liquids with solvents such as water or organic solvents varies with side chain lengths on the cation and with the choice of the anion that constitutes the ionic liquid. Examples of solvents 97 that can be used include alcohols, methylene chloride, 1-1-1 trichloroethylene, acetone, tetrahydrofuran, ethyl acetate, water, and mixtures thereof. In one embodiment, the solvent 97 comprises a mixture of an alcohol and water. In one embodiment, the solvent 97 is an alcohol, a water, or a mixture thereof. Types of alcohols that can be used include aliphatic primary alcohols, aliphatic secondary alcohols, aliphatic tertiary alcohols, and poly-alcohols, and mixtures thereof. Exemplary alcohols include, methanol, ethanol, 1-butanol, isobutanol, 2-butanol, 2-propanol, 3-pentanol, cyclo-hexanol, t-butyl alcohol, 1,3-propanediol, glycerol, and poly(ethylene glycol).

In one embodiment, the process for monitoring the chemical concentration in the ionic liquid is one wherein the solvent 97 is flowed over a face of the ATR window and particulates that have adhered to the ATR window are dissolved and washed away by the solvent 97. After the flowing of the solvent 97, the purging gas 80 is separately flowed over the face of the ATR window and the purging gas 80 dries the ATR window and lines that had previously contacted the solvent 97. These features are disclosed in FIG. 7 by the solvent flushing operation on the left and by the drying purging gas purge operation on the right.

In one embodiment, the solvent 97 cleans out residues on the ATR window. In another embodiment, the solvent 97 cleans out residues on the ATR window and lines that conduct the ionic liquid in the integrated system.

ALTERNATE EMBODIMENTS SHOWN IN THE FIGURES

The flow of the degassed ionic liquid 95 to the online FTIR instrument 400 can be intermittent or continuous. In one embodiment, the integrated system has a means for either directing the flow of the degassed ionic liquid 95 away from the ATR window or shutting off the flow to the ATR window.

FIGS. 1 & 2 demonstrate the integrated system comprising a bypass line 314, around the online FTIR instrument 400, that directs the flow of the degassed ionic liquid 95 away from the ATR window during periods when the flow of the degassed ionic liquid 95 is not passed over the ATR window. FIGS. 1 and 2 include a pump 307 and a flow element 306 between the flash drum 301 and the ATR window. The pump 307 and flow element 306 control and supply the flow of the degassed ionic liquid 95 to either the bypass line 314, the flow-through line 405, or the flow-through cell. In FIGS. 1 & 2 the flow of the degassed ionic liquid 95 to the online FTIR instrument 400 is continuous.

FIGS. 1 & 3 demonstrates the online FTIR instrument 400 comprising a flow-through cell. In one embodiment, the flow-through cell has an angled injector line and an angled return line that directs the flow of the degassed ionic liquid 95 across the ATR window in a manner that deflects particulates and reduces their accumulation on the ATR window. In one embodiment, the flow-through cell comprises a cap that connects to the ATR window and the cap comprises the angled injector line and the angled return line. In one embodiment, the angled injector line is configured to provide a liquid linear velocity greater than 0.5 ft/s (15.24 centimeters/second), such as from 1.0 ft/s (30.48 centimeters/second) to 20 ft/s (609.6 centimeters/second). Configured to can refer to one or more features of the angled injector line, such as the diameter, the surface smoothness, and the amount of pressure that can be tolerated in the angled injector line, for example. The liquid linear velocity can be adjusted and controlled to provide self-cleaning of the ATR window and extend the time of normal operation. To increase the liquid linear velocity, a dip tube can be installed in the angled injector tube to increase the liquid linear velocity and better direct the flow of the degassed ionic liquid 95 to the ATR window. In one embodiment, the online FTIR instrument 400 comprises a flow-through cell having an angled injector line and an angled return line, wherein the angled injector line is configured to provide a liquid linear velocity from 1.0 ft/s (30.48 centimeters/second) to 20 ft/s (609.6 centimeters/second) and is angled such that it directs the flow of the degassed ionic liquid 95 to the ATR window of the online FTIR instrument 400 and provides self-cleaning. Suitable angles that can be used to direct the flow of the degassed ionic liquid to the ATR window can be from 5 degrees to less than 90 degrees, such as from 15 to 45 degrees.

FIG. 1 demonstrates an embodiment of the process disclosed herein, wherein the passing of the degassed ionic liquid 95 is performed by directing the degassed ionic liquid 95 through the flow-through cell, on the online FTIR instrument 400, wherein the flow-through cell has an angled injector line and an angled return line. In one embodiment, the degassed ionic liquid 95 passes through the flow-through cell at a liquid linear velocity greater than 0.5 ft/s (15.24 centimeters/second), such as from 1.0 ft/s (30.48 centimeters/second) to 20 ft/s (609.6 centimeters/second). The process having the flow of the degassed ionic liquid 95 to the ATR window at an angle at high liquid linear velocity provides self-cleaning of the ATR window.

FIG. 2 demonstrates an integrated system wherein the online FTIR instrument 400 comprises a FTIR probe 401 with an ATR window that is inserted into the flow of the degassed ionic liquid 95. In one embodiment the FTIR probe 401 is a fiber optic ATR accessory designed for analyzing a wide range of samples in the mid-infrared. A fiber optic cable 403 can connect the FTIR probe 401 to the FTIR spectrometer and the FTIR spectrometer can be located up to 5 meters from the FTIR probe 401. Examples of online FTIR instruments comprising a FTIR probe 401 are the Diamond ATR Probes supplied by Harrick Scientific Products or ReactIR 45P HL Process FTIR supplied by Mettler Toledo.

FIG. 3 demonstrates another embodiment of an integrated online FTIR system comprising an on-off valve 312 in the sample conditioning station 300 that periodically shuts off the flow of the degassed ionic liquid to the ATR window. Unlike in FIGS. 1 and 3, wherein ionic liquid is fed continuously to the integrated online FTIR system, ionic liquid is fed intermittently in this embodiment by opening and closing the on-off valve 312 periodically to introduce a fixed volume of the ionic liquid to the flash drum 301. Examples of volumes to be sent to the flash drum 301 can be from 0.01 liters to 10 liters. A relief head valve 313 on the top of the flash drum 301 is left open, and a purging gas 80 (e.g., nitrogen) under low pressure is purged through the flash drum 301 for from 10 seconds to 30 minutes, until all of the light hydrocarbons are vaporized and flushed out of the flash drum 301. Low pressure in this embodiment, can be from 5 to 100 psig. The relief head valve 313 can then be closed and pressure can build up in the flash drum 301. When the pressure that builds up in the flash drum 301 is sufficiently higher than a return system pressure, three-way valves 309 on the inlet and outlet of the online FTIR instrument 400 are then switched on. The pressure that builds up in the flash drum 301 can then push the ionic liquid from the flash drum 301 to the ATR window in the online FTIR instrument 400, and then the ionic liquid return 700 from the online FTIR instrument 400 can be fed to a larger ionic liquid stream in the integrated system, (e.g., an ionic liquid surge drum 710 or a main system ionic liquid 205). When the ionic liquid in the flash drum is emptied as indicated by the level indicator 305, three-way valves 309 on the inlet and outlet of the online FTIR instrument 400 are switched off. Relief head valve 313 on the top of the flash drum 301 is then switched open, followed by switching on the on-off valve 312, repeating the sequence described above to monitor the chemical concentration in the ionic liquid. A feature of this embodiment is that there is no need for a pump 307 and a flow element 306 in a line between the flash drum 301 and the ATR window, which can reduce costs of equipment, maintenance, and operation.

FIGS. 1-3, and 6-8, also show the integrated system additionally comprising a validation ionic liquid reservoir 317, fluidly connected to the online FTIR instrument 400, from which is intermittently fed a validation ionic liquid 96 to the online FTIR instrument 400 while the flow of the degassed ionic liquid is directed away from the ATR window, and while the solvent flushing system 330 is closed off from the integrated system. In a flushing-validation operation of the integrated system, the used ionic liquid 90 continues to be stopped from flowing forward towards the online FTIR instrument 400, a purging gas 80 is directed to the validation ionic liquid reservoir 317 containing a validation ionic liquid 96, the validation ionic liquid 96 is directed to the online FTIR instrument 400, and the validation ionic liquid 96 is used to effectively verify a cleanliness of the integrated system, including the ATR window, and a calibration of the online FTIR instrument 400. In one embodiment, the process for monitoring the chemical concentration in the ionic liquid additionally comprises validating a calibration of the online FTIR instrument using a validation ionic liquid 96 with a known value of the chemical concentration during the periodically redirecting step c). FIGS. 1-3, and 6-8 demonstrate the integrated system, wherein a sample feed line to the online FTIR instrument 400 is located at the bottom of a hydrocarbon/ionic liquid separator 200. Taking the sample of the ionic liquid at this location and feeding it to the online FTIR instrument 400 can provide a calculated value for the chemical concentration quickly, enabling a rapid response to any process upsets in a hydrocarbon conversion unit in the integrated system using the ionic liquid. In some embodiments, the calculated value for the chemical concentration can be made in less than 30 minutes, such as in less than 10 minutes, or from 0.5 to 29 minutes from the time the ionic liquid passes over the ATR window.

FIGS. 1-3, and 6-8 demonstrate the integrated system comprising a data link 910 connecting the online FTIR instrument 400 to a computer 920. In one embodiment the data link 910 can be an Ethernet cable or a Wi-Fi network. In one embodiment, the computer 920 is in a separate analyzer building 930 from a location of the online FTIR instrument 400. In one embodiment, as shown in FIG. 2, the online FTIR instrument 400 is located together with the computer 920 in a separate analyzer building 930.

In one embodiment, the computer 920 is connected via a data link 910 to a converter 921, and the converter 921 connects via a data link 910 to a DCS 922. In one embodiment, the converter 921 is a 4 to 20 mA converter.

In one embodiment, the hydrocarbon/ionic liquid separator 200 comprises a bulk settler and a coalescer. In one embodiment, the hydrocarbon/ionic liquid separator 200 is an integrated coalescing system for separating a dispersed ionic liquid from a liquid hydrocarbon, comprising:

a) at least one bulk settler, that receives an emulsion comprising the dispersed ionic liquid with a wide range of droplet sizes ranging from small droplets less than 20 microns to large droplets greater than 500 microns, and that separates the emulsion into a clean ionic liquid phase, that is essentially free of the liquid hydrocarbon, and into a separated liquid hydrocarbon phase comprising retained ionic liquid droplets;

b) at least one pre-coalescer connected to the at least one bulk settler that receives the separated liquid hydrocarbon phase, separates out solid particles from the separated liquid hydrocarbon phase, and begins to form coalesced droplets of the retained ionic liquid droplets; and c) at least one coalescer that is fluidly connected to the at least one pre-coalescer and receives an effluent from the at least one pre-coalescer, wherein the at least one coalescer comprises multiple layers of media having a fine pore size of 20 microns or less, and produces a clean hydrocarbon stream that is essentially free of the dispersed ionic liquid and additional amounts of the clean ionic liquid phase. The clean ionic liquid phase can be the ionic liquid that is degassed in the sample conditioning station 300.

In one embodiment, the integrated system operates continuously. Continuous operation is shown in FIGS. 1 & 2. In another embodiment, the integrated system operates intermittently. Intermittent operation is shown in FIG. 3.

One benefit that can be achieved with the processes and integrated systems of this disclosure is a conservation of the used ionic liquid 90. Because the used ionic liquid 90 remains in the integrated system and is regenerated and recycled, there can be reduced amounts of fresh ionic liquid that needs to be added to the integrated system and there can also be reductions in waste used ionic liquid that needs to be disposed of or discarded.

Ionic Liquids:

In one embodiment, the ionic liquid has negligible vapor pressure and has high thermal stability. The ionic liquids, in one embodiment, encompass liquids having organic cations and inorganic or organic anions. The ionic liquids can comprise bulky asymmetric organic cations such as 1-alkyl-3-methylimidazolium, 1-alkylpyridinium, N-methyl-N-alkylpyrrolidinium or ammonium ions and a wide range of anions. Many ionic liquids are phosphonium salts. Phosphonium salts can be more thermally stable than the corresponding ammonium salts and imidazolium salts, however any can be used in the present invention.

Non-limiting examples of suitable anions include tetrafluoroborate, hexafluorophosphate, hexafluoroarsenoate, acetate, perchlorate, trifluoromethanesulfonate, trifluoroacetate, nitrate, mesylate, bis(trifluoromethylsulfonyl) imide, and thiosaccharin. Non-limiting examples of suitable cations include ammonium, imidazolium, pyridinium, piperidinium and pyrrolidinium derivatives. The ionic liquid can, in some embodiments, include a combination of any one of the above anions and any one of the above cations. For example, in some embodiments, the ionic liquid comprises an imidazolium ion (e.g., a substituted imidazolium ion). Non-limiting examples of imidazolium ions include 1-Butyl-3-methylimidazolium, 1-Ethyl-3-methylimidazolium, and 1-Hexyl-3-methylimidazolium. In some cases, the anion that forms the ionic liquid in combination with the imidazolium cation can be tetrafluoroborate, hexafluorophosphate, or bis(trifluoromethanesulfone)imide.

Examples of some other ionic liquids useful for the present invention include, but are not limited to, those ionic liquids listed and described in U.S. Pat. No. 9,238,193, US20150133711, and US20160096784 to Lei et. al., that are effective for capturing gaseous components from a process stream. In one embodiment, the ionic liquid comprises a cation, an anion, a Ag(I) salt, a Cu(I) salt, or combinations thereof. In an embodiment, the ionic liquid can reversibly capture, such as absorb, a gaseous component in a process stream. Some examples of gaseous components in a process stream that can be captured by the ionic liquid include $H_2S$, $CO_2$, RSH, $CS_2$, COS, $SO_2$, $H_2O$, ethane, propane, isobutane, ethylene, and propylene. In one embodiment, the ionic liquid performs ethylene absorption in the integrated system.

Acidic Ionic Liquids:

The most common acidic ionic liquids are those prepared from organic-based cations and inorganic or organic anions. Many of these acidic ionic liquids are ionic liquid catalysts for hydrocarbon conversions. Ionic liquid catalysts are used in a wide variety of reactions, including Friedel-Crafts reactions.

The acidic ionic liquid is composed of at least two components which form a complex. The acidic ionic liquid comprises a first component and a second component. The first component of the acidic ionic liquid will typically comprise a Lewis acid compound selected from components such as Lewis acid compounds of Group 13 metals, including aluminum halides, alkyl aluminum dihalides, gallium halide, and alkyl gallium halide (see the Periodic Table, which defines the elements that are Group 13 metals). Other Lewis acid compounds besides those of Group 13 metals may also be used. In one embodiment the first component is aluminum halide or alkyl aluminum dihalide. For example, aluminum trichloride ($AlCl_3$) may be used as the first component for preparing the ionic liquid catalyst. In one embodiment, the alkyl aluminum dihalides that can be used can have the general formula $Al_2X_4R_2$, where each X represents a halogen, selected for example from chlorine and bromine, each R represents a hydrocarbyl group comprising 1 to 12 atoms of carbon, aromatic or aliphatic, with a branched or a linear chain. Examples of alkyl aluminum dihalides include dichloromethylaluminum, dibromomethylaluminum, dichloroethylaluminum, dibromoethylaluminum, dichloro n-hexylaluminum, dichloroisobutylaluminum, either used separately or combined.

The second component making up the acidic ionic liquid is an organic salt or mixture of salts. These salts may be characterized by the general formula $Q^+A^-$, wherein $Q^+$ is an ammonium, phosphonium, boronium, oxonium, iodonium, or sulfonium cation and $A^-$ is a negatively charged ion such as $Cl^-$, $Br^-$, $ClO_4^-$, $NO_3^-$, $BF_4^-$, $BCl_4^-$, $PF_6^-$, $SbF_6^-$, $AlCl_4^-$, $Al_2Cl_7^-$, $Al_3Cl_{10}^-$, $GaCl_4^-$, $Ga_2Cl_7^-$, $Ga_3Cl_{10}^-$, $AsF_6^-$, $TaF_6^-$, $CuCl_2^-$, $FeCl_3^-$, $AlBr_4^-$, $Al_2Br_7^-$, $SO_3CF_3^-$, and 3-sulfurtrioxyphenyl. In one embodiment the second component is selected from those having quaternary ammonium halides containing one or more alkyl moieties having from about 1 to about 9 carbon atoms, such as, for example, trimethylammonium hydrochloride, methyltributylammonium, 1-butyl pyridinium, or alkyl substituted imidazolium halides, such as for example, 1-ethyl-3-methyl-imidazolium chloride.

In one embodiment, the acidic ionic liquid comprises a monovalent cation selected from the group consisting of a pyridinium ion, an imidazolium ion, a pyridazinium ion, a pyrazolium ion, an imidazolinium ion, a imidazolidinium ion, an ammonium ion, a phosphonium ion, and mixtures thereof. Examples of possible cations ($Q^+$) include a butylethylimidazolium cation [beim], a butylmethylimidazolium cation [bmim], butyldimethylimidazolium cation [bmmim], decaethylimidazolium cation [dceim], a decamethylimidazolium cation [dcmim], a diethylimidazolium cation [eeim], dimethylimidazolium cation [mmim], an ethyl-2,4-dimethylimidazolium cation [e-2,4-mmim], an ethyldimethylimidazolium cation [emmim], an ethylimidazolium cation [eim], an ethylmethylimidazolium [emim] cation, an ethylpropylimidazolium cation [epim], an ethoxyethylmethylimidazolium cation [etO-emim], an ethoxydimethylimidazolium cation [etO-minim], a hexadecylmethylimidazolium cation [hexadmim], a heptylmethylimidazolium cation [hpmim], a hexaethylimidazolium cation [hxeim], a hexamethylimidazolium cation [hxmim], a hexadimethylimidazolium cation [hxmmim], a methoxyethylmethylimidazolium cation [meO-emim], a methoxypropylmethylimidazolium cation [meO-prmim], a methylimidazolium cation [mim], dimethylimidazolium cation [mmim], a methylnonylimidazolium cation [mnim], a methylpropylimidazolium cation [mpim], an octadecylmethylimidazolium cation [octadmim], a hydroxylethylmethylimidazolium cation [OH-emim], a hydroxyloctylmethylimidazolium cation [OH-omim], a hydroxylpropylmethylimidazolium cation [OH-prmim], an octylmethylimidazolium cation [omim], an octyldimethylimidazolium cation [ommim], a phenylethylmethylimidazolium cation [ph-emim], a phenylmethylimidazolium cation [ph-mim], a phenyldimethylimidazolium cation [ph-minim], a pentylmethylimidazolium cation [pnmim], a propylmethylimidazolium cation [prmim], a 1-butyl-2-methylpyridinium cation[1-b-2-mpy], 1-butyl-3-methylpyridinium cation[1-b-3-mpy], a butylmethylpyridinium [bmpy] cation, a 1-butyl-4-dimethylacetylpyridinium cation [1-b-4-DMApy], a 1-butyl-4-methylpyridinium cation[1-b-4-mpy], a 1-ethyl-2-methylpyridinium cation[1-e-2-mpy], a 1-ethyl-3-methylpyridinium cation[1-e-3-mpy], a 1-ethyl-4-dimethylacetylpyridinium cation[1-e-4-DMApy], a 1-ethyl-4-methylpyridinium cation[1-e-4-mpy], a 1-hexyl-4dimethylacetylpyridinium cation[1-hx-4-DMApy], a 1-hexyl-4-methylpyridinium cation[1-hx-4-mpy], a 1-octyl-3-methylpyridinium cation[1-o-3-mpy], a 1-octyl-4-methylpyridinium cation[1-o-4-mp y], a 1-propyl-3-methylpyridinium cation[1-pr-3-mpy], a 1-propyl-4-methylpyridinium cation[1-pr-4-mpy], a butylpyridinium cation [bpy], an ethylpyridinium cation [epy], a heptylpyridinium cation [hppy], a hexylpyridinium cation [hxpy], a hydroxypropylpyridinium cation [OH-prpy], an octylpyridinium cation [opy], a pentylpyridinium cation [pnpy], a propylpyridinium cation [prpy], a butylmethylpyrrolidinium cation [bmpyr], a butylpyrrolidinium cation [bpyr], a hexylmethylpyrrolidinium cation [hxmpyr], a hexylpyrrolidinium cation [hxpyr], an octylmethylpyrrolidinium cation [ompyr], an octylpyrrolidinium cation [opyr], a propylmethylpyrrolidinium cation [prmpyr], a butylammonium cation [b-N], a tributylammonium cation [bbb-N], a tetrabutylammonium cation [bbbb-N], a butylethyldimethylammonium cation [bemm-N], a butyltrimethylammonium cation [bmmm-N], a N,N,N-trimethylethanolammonium cation [choline], an ethylammonium cation [e-N], a diethylammonium cation [ee-N], a tetraethylammonium cation [eeee-N], a tetraheptylammonium cation [hphphphp-N], a tetrahexylammonium cation [hxhxhxhx-N], a methylammonium cation [m-N], a dimethylammonium cation [mm-N], a tetramethylammonium cation [mmmm-N], an ammonium cation [N], a butyldimethylethanolammonium cation [OHe-bmm-N], a dimethylethanolammonium cation [OHe-mm-N], an ethanolammonium cation [OHe-N], an ethyldimethylethanolammonium cation [OHe-emm-N], a tetrapentylammonium cation [pnpnpnpn-N], a tetrapropylammonium cation [prprprpr-N], a tetrabutylphosphonium cation [bbbb-P], a tributyloctylphosphonium cation [bbbo-P], or combinations thereof.

In one embodiment, the second component is selected from those having quaternary phosphonium halides containing one or more alkyl moieties having from 1 to 12 carbon atoms, such as, for example, trialkyphosphonium hydrochloride, tetraalkylphosphonium chlorides, and methyltrialkyphosphonium halide.

In one embodiment, the acidic ionic liquid comprises an unsubstituted or partly alkylated ammonium ion.

In one embodiment, the acidic ionic liquid is chloroaluminate or a bromoaluminate. In one embodiment the acidic ionic liquid is a quaternary ammonium chloroaluminate ionic liquid having the general formula RR' R" N H+ $Al_2Cl_7^-$, wherein R, R', and R" are alkyl groups containing 1 to 12 carbons. Examples of quaternary ammonium chloroaluminate ionic liquids are an N-alkyl-pyridinium chloroaluminate, an N-alkyl-alkylpyridinium chloroaluminate, a pyridinium hydrogen chloroaluminate, an alkyl pyridinium hydrogen chloroaluminate, a di alkyl-imidazolium chloroaluminate, a tetra-alkyl-ammonium chloroaluminate, a tri-alkyl-ammonium hydrogen chloroaluminate, or a mixture thereof.

The presence of the first component should give the acidic ionic liquid a Lewis or Franklin acidic character. Generally, the greater the mole ratio of the first component to the second component, the greater is the acidity of the acidic ionic liquid.

For example, a typical reaction mixture to prepare n-butyl pyridinium chloroaluminate ionic liquid is shown below:

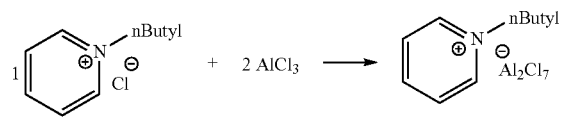

In one embodiment, the acidic ionic liquid is used as a catalyst for a hydrocarbon conversion and the hydrocarbon conversion utilizes a co-catalyst to provide enhanced or improved catalytic activity. A co-catalyst can comprise, for example, anhydrous hydrogen chloride or organic chloride (see, e.g., U.S. Pat. No. 7,495,144 and U.S. Pat. No. 7,531,707). When organic chloride is used as the co-catalyst with the acidic ionic liquid, hydrogen chloride may be formed in situ in the apparatus either during the hydrocarbon conversion process or during post-processing of the output of the hydrocarbon conversion. In one embodiment, the hydrocarbon conversion is conducted in the presence of a hydrogen halide, e.g., HCl. In one embodiment, the hydrogen chloride is recycled from a downstream operation, which reduces the amount of the organic chloride that is injected into the acidic ionic liquid to promote the acidic ionic liquid catalyst activity.

When used in a hydrocarbon conversion by an acidic ionic liquid catalyst, the alkyl halide additive or the hydrogen halide are used in catalytic amounts. In one embodiment, the amounts of the alkyl halide or hydrogen halide should be kept at low concentrations and not exceed the molar concentration of an $AlCl_3$ in the acidic ionic liquid. For example, the amounts of the alkyl halide additive or the hydrogen halide used may range from 0.001 mol % to 100 mol % of the Lewis acid (e.g., $AlCl_3$) in the acidic ionic liquid in order to keep the acidity of the acidic ionic liquid catalyst at the desired performing capacity. The amount of the alkyl halide that may be required can be a lower mol % of the Lewis acid in the acidic ionic liquid when an alkyl halide that comprises a higher wt % of halide is used.

In one embodiment, the amount or type of the halide containing additive that is fed via one or more injection quills into an immiscible catalyst feed to the hydrocarbon conversion reactor or the hydrocarbon conversion unit can be adjusted to change product selectivity in downstream operations in response to a measured conjunct polymer concentration in the acidic ionic liquid. The effective stable control and adjustments of the amounts of these immiscible liquid streams (halide containing additive and catalyst feed 30) is achieved by the integrated systems and processes of this disclosure.

Hydrocarbon Conversion Using Acidic Ionic Liquids

Acidic ionic liquids can be used as catalysts for various types of hydrocarbon conversions. Examples of these hydrocarbon conversions include: an alkylation, a dimerization, an oligomerization, an acylation, a hydrocracking, a metathesis, a copolymerization, an isomerization, a carbonylation, a hydroformylation, a dehalogenation, a dehydration, a disproportionation, a transalkylation, and combinations thereof. In one embodiment, the hydrocarbon conversion is alkylation of paraffins with olefins. In another embodiment, the hydrocarbon conversion is alkylation of aromatics. Examples of ionic liquid catalysts and their use for alkylation of paraffins with olefins are taught, for example, in U.S. Pat. Nos. 7,432,408, 7,432,409, 7,285,698, and 7,923,593. In one embodiment, the acidic ionic liquid is a composite ionic liquid catalyst, wherein the cations come from a hydrohalide of an alkyl-containing amine or pyridine, and the anions are composite coordinate anions coming from two or more metal compounds. In another embodiment the conversion of a hydrocarbon is alkylation of paraffins, alkylation of aromatics, or combinations thereof.

In one embodiment, the feed to the hydrocarbon conversion comprises at least one olefin and at least one isoparaffin. For example the feed can comprise a mixture of at least one mostly linear olefin from $C_2$ to about $C_{30}$. In another embodiment, the feed can comprise at least 50% of a single alpha olefin species. In one embodiment, the olefin feed 10 comprises at least one isomerized olefin.

In one embodiment, the feed to an alkylation reactor 100 used for the hydrocarbon conversion by an acidic ionic liquid catalyst comprises one or more $C_4$-$C_7$ isoparaffins and one or more $C_2$-$C_5$ olefins, and the process produces an alkylate gasoline blending component.

In one embodiment, the feed to the hydrocarbon conversion comprises isobutane. In one embodiment, isopentanes, isohexanes, isoheptanes, and other higher isoparaffins up to about $C_{30}$ are also useable in the processes and integrated systems disclosed herein. Mixtures of light isoparaffins can also be used. Mixtures such as $C_3$-$C_4$, $C_3$-$C_5$, or $C_4$-$C_5$ isoparaffins can also be used and may be advantaged because of reduced separation costs.

In one embodiment, the feed to the hydrocarbon conversion can also contain diluents such as normal paraffins. This can be a cost savings by reducing the cost of separating isoparaffins from close boiling paraffins. In one embodiment, the normal paraffins will tend to be unreactive diluents in the hydrocarbon conversion.

Figure 4:
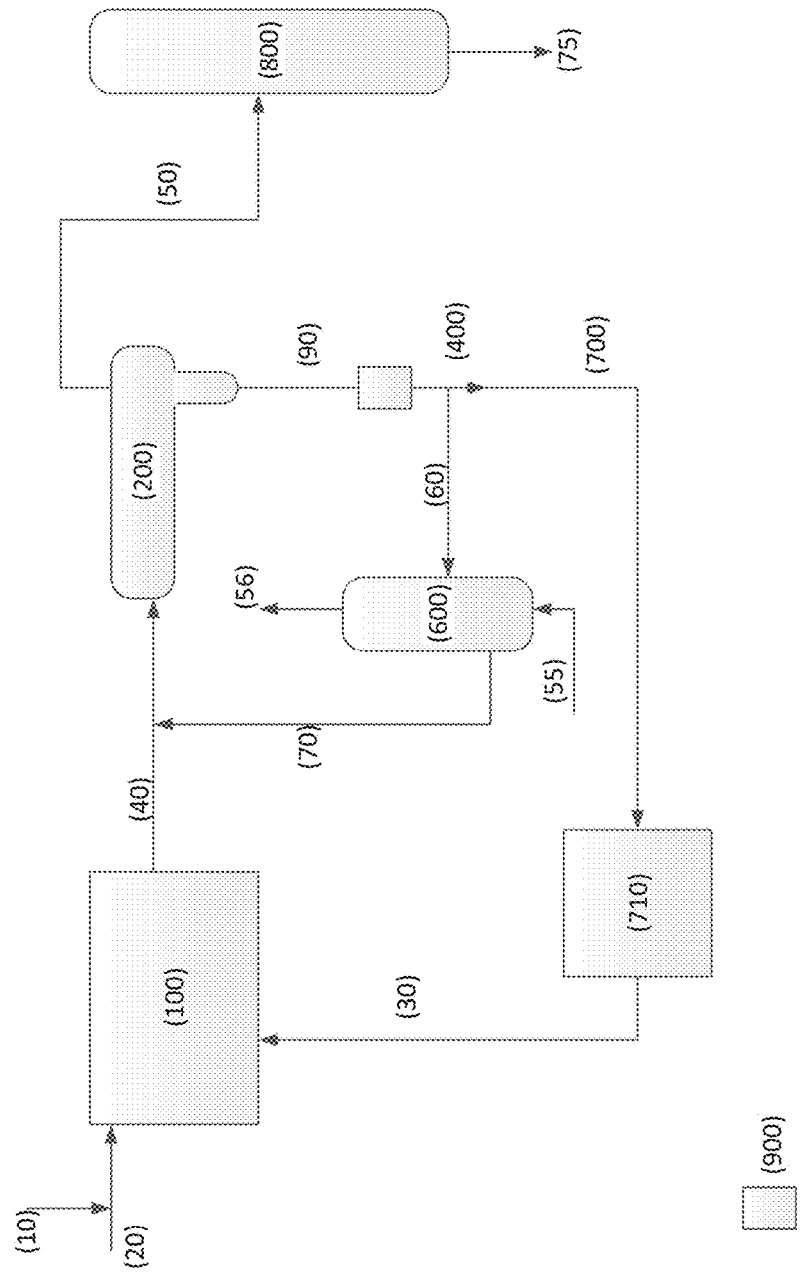
FIG. 4 is a process flow diagram of a refinery alkylation unit with an exemplary embodiment of the integrated system with the placement of an online FTIR instrument in the unit.

An embodiment of an integrated system is shown in FIG. 4. The features shown in FIG. 4 include an olefin feed 10 and an isobutane feed 20, being fed to an alkylation reactor 100. A catalyst feed 30 is also fed to the alkylation reactor 100. A reactor effluent 40 is passed to a hydrocarbon/ionic liquid separator 200 that separates the reactor effluent 40 into the used ionic liquid 90 and the separated hydrocarbons 50. The separated hydrocarbons 50 are further separated into fractions in a distillation column 800. An alkylate 75 is withdrawn from the lower portion of the distillation column 800. A first portion of the used ionic liquid 90 is passed, as regeneration feed 60, to a regeneration reactor 600 that uses hydrogenation to regenerate the regeneration feed 60. Hydrogen feed 55 is fed to the regeneration reactor 600 and a hydrogen outlet 56 removes the remaining hydrogen from the regeneration reactor 600. The regeneration effluent 70 is recycled and mixed with the reactor effluent 40 and this combined stream goes to the hydrocarbon/ionic liquid separator 200. A second portion of the used ionic liquid 90, the ionic liquid return 700, is fed to an ionic liquid surge drum 710. The ionic liquid surge drum 710 is the source of the catalyst feed 30. The online FTIR instrument 400, or a sampling location that takes a sample of the used ionic liquid 90 for FTIR analysis, is placed between the hydrocarbon/ionic liquid separator 200 and the regeneration reactor 600. Also shown, in FIG. 4, is a separate offline FTIR instrument 900 that is used in a comparative example (Example 1) in this disclosure.

In one embodiment, the chemical concentration being monitored in the integrated system is related to the activity of the ionic liquid for performing a hydrocarbon conversion or a gas absorption in the integrated system. The chemical concentration being monitored, for example, can include conjunct polymers, absorbed gasses, anion species, or combinations thereof, in the ionic liquid.

In one embodiment, in the process for monitoring the chemical concentration in the ionic liquid, the ionic liquid being tested is a slipstream from a continuous operation of the process unit utilizing the ionic liquid. This feature is shown in FIGS. 1-3. The slipstream of the ionic liquid is what is degassed in the sample conditioning station 300 and subsequently passed over the ATR window of the online FTIR instrument 400.

In one embodiment, the integrated system comprises automatic valves that switch between different modes of operation. The automatic valves can be programmed to switch between the modes based on selected timing, or in response to the chemical concentration that falls outside of a set range.

In one embodiment, a tubing in the integrated system is arranged to minimize high and low points to avoid material accumulations in the high and low points. In one embodiment, the tubing in the integrated system has a number of high and low points minimized. The tubing should have less than ten high and low points. For example, the tubing can have from zero to five high and low points and thus avoids material accumulations in said high and low points. Minimizing the number of high and low points in the tubing can provide more accurate monitoring of the chemical concentration in the ionic liquid.

In one embodiment, the online FTIR instrument 400 is installed in an analyzer building 930. In one embodiment, the online FTIR instrument 400 is installed inside a cabinet enclosure that is equipped with a heater, that provides temperature control, and a nitrogen purging system to meet requirements of a Class I, Division 2 field environment. Requirements for Class I, Division 2 field environments are defined in US Regulations Standards—29 CFR, Part 1910.307. A Class I, Division 2 location is a location:

(i) In which volatile flammable liquids or flammable gases are handled, processed, or used, but in which the hazardous liquids, vapors, or gases will normally be confined within closed containers or closed systems from which they can escape only in the event of accidental rupture or breakdown of such containers or systems, or as a result of abnormal operation of equipment; or (ii) In which ignitable concentrations of gases or vapors are normally prevented by positive mechanical ventilation, and which might become hazardous through failure or abnormal operations of the ventilating equipment; or (iii) That is adjacent to a Class I, Division 1 location, and to which ignitable concentrations of gases or vapors might occasionally be communicated unless such communication is prevented by adequate positive-pressure ventilation from a source of clean air, and effective safeguards against ventilation failure are provided. The cabinet enclosure can be located, for example, in the sample conditioning station 300 or in the analyzer building 930.

In one embodiment, electric heat tracing and insulation are applied to a tubing in the integrated system. Heat tracing can be used to maintain or raise the temperature of pipes, lines, and vessels in the integrated system. An electrical heating element can be run, for example, in physical contact along the length of a pipe. The pipe will then be covered with thermal insulation to retain heat losses from the pipe. Heat generated by the element then maintains the temperature of the pipe. Heat tracing may be used to protect pipes from freezing, to maintain a constant flow temperature, or to maintain process temperatures for piping that transports substances that can solidify at ambient temperatures. Electric heat tracing cables are an alternative to steam trace heating where steam is not available or unwanted.

The transitional term "comprising", which is synonymous with "including," "containing," or "characterized by," is inclusive or open-ended and does not exclude additional, unrecited elements or method steps. The transitional phrase "consisting of" excludes any element, step, or ingredient not specified in the claim. The transitional phrase "consisting essentially of" limits the scope of a claim to the specified materials or steps "and those that do not materially affect the basic and novel characteristic(s)" of the claimed invention.

For the purposes of this specification and appended claims, unless otherwise indicated, all numbers expressing quantities, percentages or proportions, and other numerical values used in the specification and claims, are to be understood as being modified in all instances by the term "about." Furthermore, all ranges disclosed herein are inclusive of the endpoints and are independently combinable. Whenever a numerical range with a lower limit and an upper limit are disclosed, any number falling within the range is also specifically disclosed. Unless otherwise specified, all percentages are in weight percent.

Any term, abbreviation or shorthand not defined is understood to have the ordinary meaning used by a person skilled in the art at the time the application is filed. The singular forms "a," "an," and "the," include plural references unless expressly and unequivocally limited to one instance.

All of the publications, patents and patent applications cited in this application are herein incorporated by reference in their entirety to the same extent as if the disclosure of each individual publication, patent application or patent was specifically and individually indicated to be incorporated by reference in its entirety.

This written description uses examples to disclose the invention, including the best mode, and also to enable any person skilled in the art to make and use the invention. Many modifications of the exemplary embodiments of the invention disclosed above will readily occur to those skilled in the art. Accordingly, the invention is to be construed as including all structure and methods that fall within the scope of the appended claims. Unless otherwise specified, the recitation of a genus of elements, materials or other components, from which an individual component or mixture of components can be selected, is intended to include all possible subgeneric combinations of the listed components and mixtures thereof.

The invention illustratively disclosed herein suitably may be practiced in the absence of any element which is not specifically disclosed herein.

EXAMPLES

Example 1 (Comparative): Preliminary In Situ Monitoring of Conjunct Polymer

In a pilot plant alkylation unit using an acidic ionic liquid to make alkylate gasoline blending components, a flow-through FTIR ATR instrument was installed at the effluent of a separation unit that separated hydrocarbons from the ionic liquid. The ionic liquid used in the unit was n-butyl pyridinium chloroaluminate ionic liquid. The flow-through FTIR ATR instrument was modified by fitting it with a cap, having O-ring seals and two angled tubes, that was screwed onto the top of the ATR window such that the ionic liquid continuously flushed the ATR window under the process pressure. The linear velocity of the ionic liquid through the flow-through FTIR ATR instrument was about 0.30 ft/s (about 9.144 centimeters/second) to about 0.40 ft/s (about 12.19 centimeters/second).

The configuration of the test unit used for this comparative example is shown in FIG. 4. The online flow-through FTIR ATR instrument was placed directly downstream of the hydrocarbon/ionic liquid separator 200 in the integrated system in order to get a quick indication of the dynamics of the pilot plant alkylation unit operation.

FTIR ATR measurements were taken by the flow-through FTIR ATR instrument and compared with measurements made in an offline FTIR ATR instrument in a satellite lab. Both FTIR ATR instruments were Bruker Alpha FTIRs with ATR windows. They were calibrated and operated identically. The infrared peak area at a range from 1330 to 1405 cm$^{-1}$ was integrated and plotted against known conjunct polymer concentrations, and the integrated peak area was linearly correlated with the conjunct polymer concentration with a correlation coefficient ($R^2$) of 0.999. The relation between the integrated peak area and the conjunct polymer was expressed as follows: Wt % Conjunct Polymer=−2.806+10.626×Integrated Peak Area.

Initially, the trends for the measurement of conjunct polymer concentration by the two different instruments matched fairly well. The flow-through FTIR ATR provided continuous and rapid conjunct polymer concentrations in the used ionic liquid 90 in the pilot plant alkylation unit, which captured the dynamics of the operation of the unit. After operating for about two to three weeks, however, several operating issues were observed with the flow-through FTIR ATR instrument:

1. Particulates in the ionic liquid stream fouled the ATR window in the flow-through cell and caused erratic FTIR readings; this was especially noticeable when the flow-through FTIR ATR cell was disrupted during a brief shut down of the test unit which left ionic liquid static in the flow-through cell for approximately 15 hours and accelerated the fouling. These particulates were a mixture of hydrolyzed ionic liquid and metal corrosion products that had formed in the pilot plant alkylation unit.

2. Isobutane dissolved in the ionic liquid resulted in a consistent overestimation of conjunct polymer concentration, which did not occur in the offline FTIR ATR due to the weathering of the samples during transport.

3. Foaming of the ionic liquid, believed to be associated with the dissolved isobutane, caused erratic measurements of the conjunct polymer content.

4. The flow-through FTIR ATR instrument was forced to shut down and be disassembled in order to clean up the ATR window.

Example 2: Impact of Branched Alkanes on Conjunct Polymer Measurements

Figure 5:
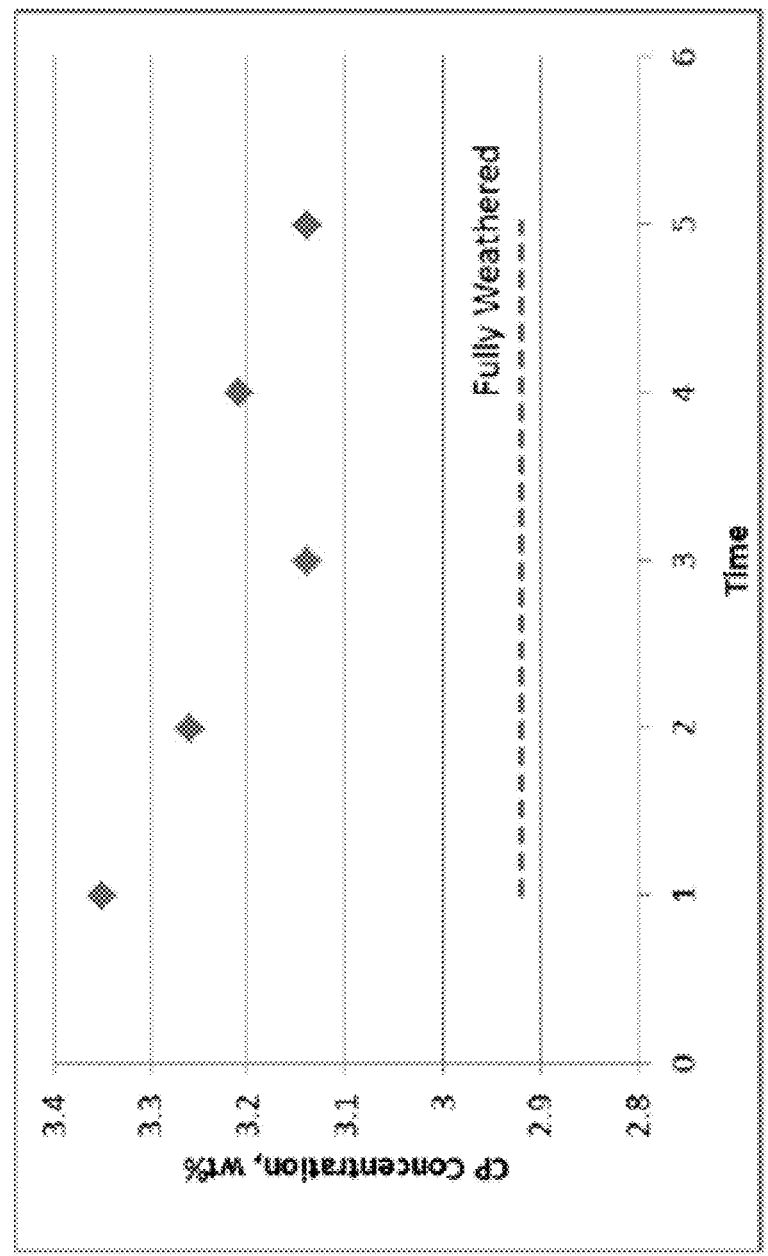
FIG. 5 is a graph of the conjunct polymer concentration measurements made on an initially frozen used ionic liquid sample from an alkylation unit and a fully weathered ionic liquid sample from the same alkylation unit.

A sample of used ionic liquid 90 taken from the pilot plant alkylation unit described in Example 1, under system pressure, was cooled in a freezer and then dripped onto the FTIR ATR window in the offline FTIR ATR instrument in the satellite lab. The FTIR ATR instrument continuously measured the integrated peak area and calculated the conjunct polymer concentration, as described in Example 1. The measured conjunct polymer concentration dropped as the sample of the used ionic liquid 90 warmed up and isobutane vaporized to the atmosphere. The results of this experiment are shown in FIG. 5.

As the isobutane vaporized, the measured conjunct polymer concentration in the used ionic liquid 90 decreased and approached the value corresponding to the final fully-weathered ionic liquid that had no isobutane remaining. The isobutane dissolved in the used ionic liquid 90 caused an overestimation of the conjunct polymer concentration in the used ionic liquid 90 when the sample was not exposed to conditions that allowed the isobutane to vaporize before the measurement was made.

Example 3: On-Line FTIR with Improved Flushing and Validation

The integrated system as shown in FIG. 1 was designed to overcome the problems identified in the pilot plant unit described previously. The online flow-through FTIR instrument is placed inside of a purged instrument cabinet 410, following a pre-filter and a 2-gallon (7.571 liters) flash drum 301 and all of these are inside a sample conditioning station 300. A slipstream off of a flow from the main system ionic liquid 205 from a hydrocarbon/ionic liquid separator 200 is sent through the pre-filter then to the flash drum 301. The pre-filter facilitates efficient de-foaming of the used ionic liquid 90 by coalescing and collapsing the foam in the used ionic liquid 90; and the pre-filter gives improved separation of the light hydrocarbons from the degassed ionic liquid 95. The pre-filter also removes particulates that can foul the ATR window in the online flow-through FTIR instrument. The flash drum 301, operating at ambient pressure, was designed to allow isobutane and any other light hydrocarbons in the used ionic liquid 90 to vaporize and be removed and to produce the degassed ionic liquid 95 to be sent to the online flow-through FTIR instrument. The flash drum 301 is fitted with a level controller 305 set to about 50% level and provides a 10 minute residence time in the flash drum 301 to provide the degassed ionic liquid 95. The flash drum 301 is outfitted with a demister pad and the gases that are flashed off are sent via a check valve 308 and a control valve to a scrubber 320. The purging gas 80 in this example is nitrogen, but other inert gases could be used.

The flow-through line 405 is ¼" tubing, and it has an inside diameter (ID) of 0.18 inch (0.4572 centimeter).

A validation ionic liquid reservoir 317, holding a validation ionic liquid 96 with a known concentration of conjunct polymer is included and can be used to periodically calibrate the online flow-through FTIR instrument.

Figure 6:
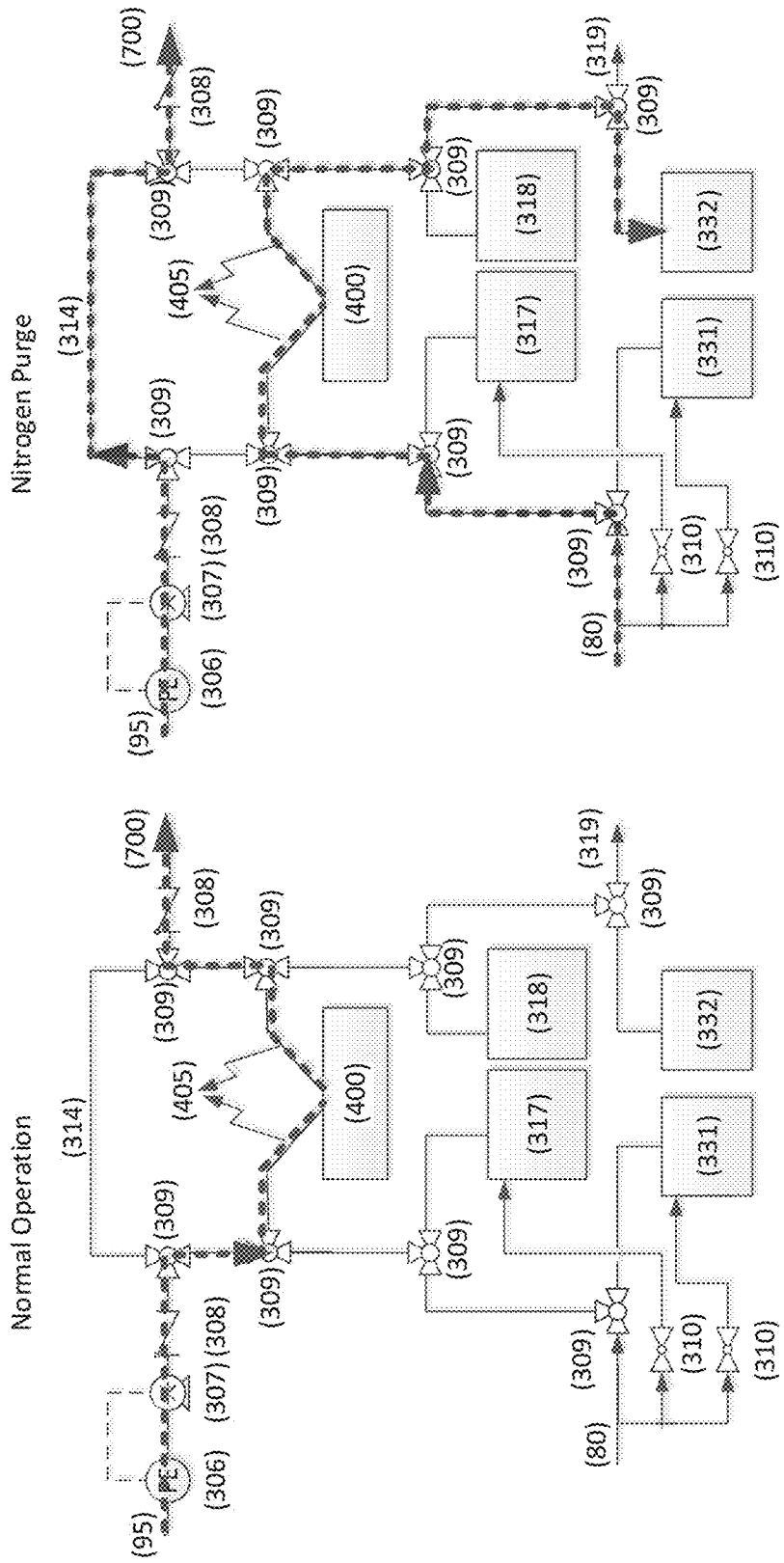
FIG. 6 includes diagrams of one integrated system of this disclosure operating in two different modes: normal operation and purging gas purge operation.
Figure 7:
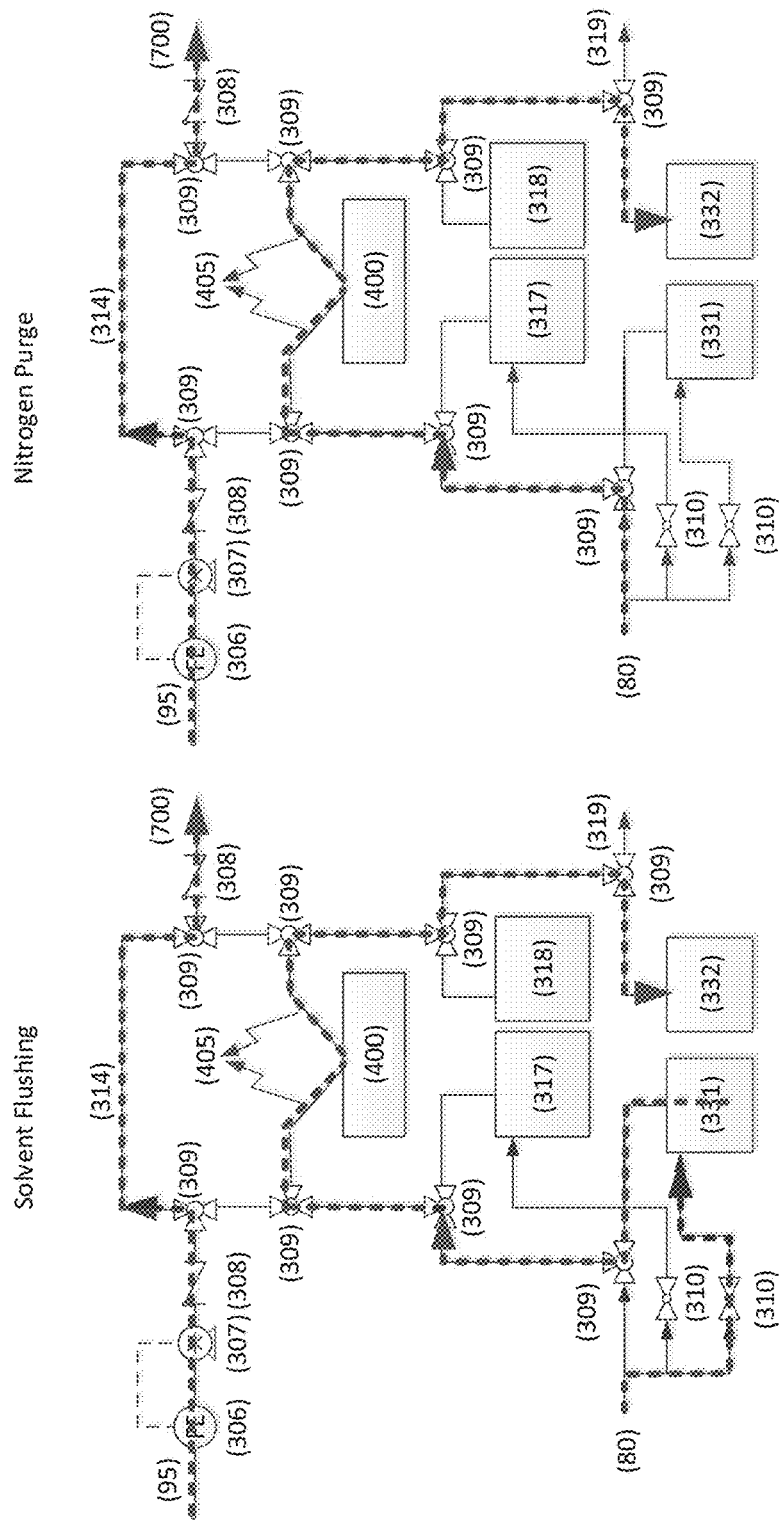
FIG. 7 includes diagrams of one integrated system of this disclosure operating in two different modes: solvent flushing operation and drying purging gas purge operation.
Figure 8:
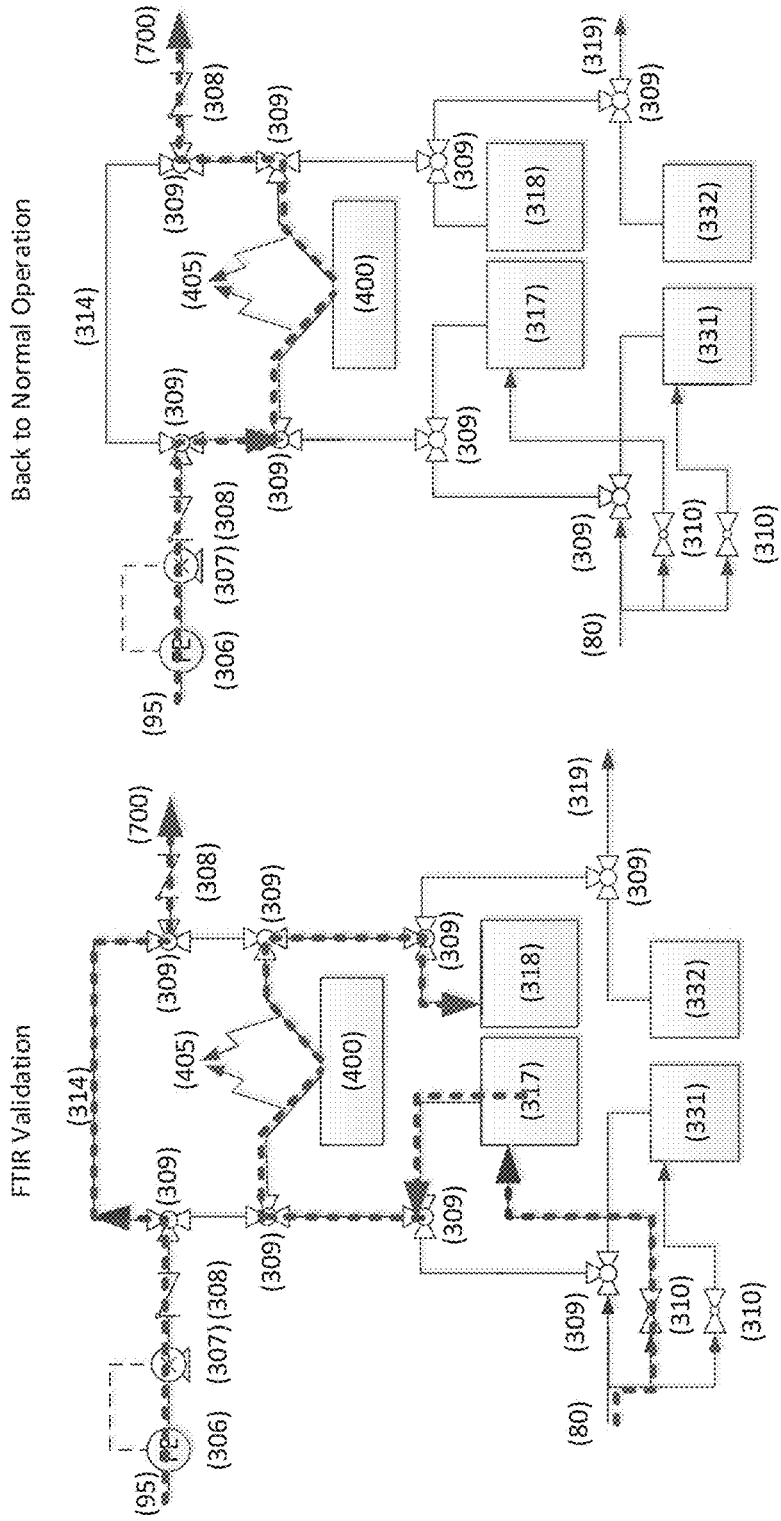
FIG. 8 includes diagrams of one integrated system of this disclosure operating in two different modes: flushing-validation operation and normal operation.

In FIGS. 6-8, different modes of operation of the integrated system are shown. The active flows in the integrated system during each mode are shown with bold dashed lines. The tubing, three way valves 309, check valves 308, and ball valves 310 can be arranged as shown in FIGS. 6-8 to allow for operating in five separate modes, as follows:

1) normal operation as shown in the left of FIG. 6, where used ionic liquid 90 flows through 3-way valves 309 and is directed to the flow-through line 405 to the on-line flow-through FTIR instrument and then onto the ionic liquid surge drum 710. The liquid linear velocity in the flow-through line 405 is about 2.8 ft/s (about 85.34 centimeters/second), which is sufficient to prevent particulate build-up on the ATR window for many hours of operation. During the normal operation, a calculated value for a conjunct polymer concentration is obtained within 0.1 to 5 minutes, or within 0.1 to 1 minute, of the flow of the degassed ionic liquid over the ATR window. Significant increases in the conjunct polymer concentration are indicative of upsets in the operation of the alkylation unit that uses the ionic liquid and these upsets can be corrected quickly.

2) purging gas purge, as shown in the right of FIG. 6, where used ionic liquid 90 flows through 3-way valves 309 that direct the flow of the used ionic liquid 90 through the bypass line 314 and then onto the ionic liquid surge drum 710. A feed of purging gas 80 purges out residual used ionic liquid to a used ionic liquid return vessel 318.

3) solvent flushing, as shown in the left of FIG. 7, where used ionic liquid 90 continues to flow through the bypass line 314 and then onto the ionic liquid surge drum 710. A feed of purging gas 80 at moderate pressure is directed to the fresh solvent reservoir 331 and the solvent 97 is thus pushed through 3-way valves 309 to the flow-through line 405 and through the online flow-through FTIR instrument to flush and clean out residues in the lines and instrument. The solvent 97 that is used in this example is a mixture of methanol and water. The used solvent 98 with the removed residues is collected in the used solvent reservoir 332.

4) drying purging gas purge, as shown in the right of FIG. 7, where used ionic liquid 90 continues to flow through the bypass line 314 and then onto the ionic liquid surge drum 710. The flow of solvent 97 is stopped, and the feed of the purging gas 80 at moderate pressure is directed via 3-way valves 309 through the conditioning purging gas line 304, through the flow-through line 405, through the online flow-through FTIR instrument, and then to vent 319. The drying purging gas purge mode of operation purges out the solvent 97 that is remaining and dries the system.

5) flushing-validation, as shown in the left of FIG. 8, where used ionic liquid 90 continues to flow through the bypass line 314 and then onto the ionic liquid surge drum 710. The purging gas 80, fed at moderate pressure, is directed via a ball valve 310 to the validation ionic liquid reservoir 317 containing validation ionic liquid 96. The validation ionic liquid 96 is directed via 3-way valves 309 through the flow-through line 405 and through the online flow-through FTIR instrument. The validation ionic liquid 96 is used to verify the cleanliness of the system and to validate the accuracy of the online flow-through FTIR instrument. The validation ionic liquid 96 also dissolves any remaining residues or impurities that might remain after the solvent flushing and drying purging gas purge steps. When cleanliness and validation are confirmed, then the system can return to its normal operation as shown in the right of FIG. 8.

It is claimed:

1. An integrated system for monitoring a chemical concentration in an ionic liquid, comprising:
   a. an online FTIR instrument with an ATR window having a flow of a degassed ionic liquid to the ATR window;
   b. a sample conditioning station comprising a flash drum, placed upstream from the ATR window, that removes light hydrocarbons from the ionic liquid and produces the degassed ionic liquid that is analyzed by the online FTIR instrument; and
   c. a solvent flushing system that intermittently flows a solvent and a purging gas across the ATR window during periods when the flow of the degassed ionic liquid is not passed over the ATR window.

2. The integrated system of claim 1, additionally comprising: a bypass line around the online FTIR instrument that directs the flow of the degassed ionic liquid away from the ATR window.

3. The integrated system of claim 1, wherein the online FTIR instrument comprises a flow-through cell having an angled injector line and an angled return line, wherein the angled injector line is configured to provide a liquid linear velocity from 30.48 centimeters/second to 609.6 centimeters/second and is angled such that it directs the flow of the degassed ionic liquid to the ATR window of the online FTIR instrument and provides self-cleaning.

4. The integrated system of claim 1, wherein the online FTIR instrument comprises a FTIR probe that is inserted into the flow of the degassed ionic liquid at an angle allowing self-cleaning by the flow of the degassed ionic liquid.

5. The integrated system of claim 1, wherein the chemical concentration is related to an activity of the ionic liquid for performing a hydrocarbon conversion or a gas absorption in the integrated system.

6. The integrated system of claim 1, wherein the sample conditioning station comprises a filter that reduces a foam in the ionic liquid and removes particulates from the ionic liquid.

7. The integrated system of claim 1, wherein the online FTIR instrument is installed inside a cabinet enclosure that is equipped to provide a temperature control and comprises a nitrogen purging system to meet requirements of a Class I, Division 2 field environment.

8. The integrated system of claim 1, additionally comprising a validation ionic liquid reservoir, fluidly connected to the online FTIR instrument, from which is intermittently fed a validation ionic liquid to the online FTIR instrument while the flow of the degassed ionic liquid is directed away from the ATR window, and while the solvent flushing system is closed off from the integrated system.

9. The integrated system of claim 1, wherein the solvent flushing system comprises a fresh solvent reservoir that is connected to a source of the purging gas and the purging gas directs a solvent flow from the fresh solvent reservoir through the online FTIR instrument.

10. The integrated system of claim 1, wherein the flash drum comprises a relief head valve that provides a low flash drum pressure in the sample conditioning station.

11. A process for monitoring a chemical concentration in an ionic liquid, comprising:

a. degassing the ionic liquid in a sample conditioning station comprising a flash drum that is fluidly connected to a process unit utilizing the ionic liquid, wherein the sample conditioning station removes light hydrocarbons from the ionic liquid and produces a degassed ionic liquid;

b. passing the degassed ionic liquid in a flow over an ATR window of an online FTIR instrument;

c. periodically redirecting the flow of the degassed ionic liquid away from the ATR window via a bypass line or an on-off valve that isolates the ATR window from the process unit that elutes the ionic liquid; and d. flowing a solvent and a purging gas over the ATR window during the periodically redirecting step c); and e. resuming the passing of the degassed ionic liquid over the ATR window.

12. The process of claim 11, wherein the passing of the degassed ionic liquid is performed by directing the degassed ionic liquid through a flow-through cell, on the online FTIR instrument, wherein the flow-through cell has an angled injector line and an angled return line, wherein the degassed ionic liquid passes through the flow-through cell at a liquid linear velocity from 30.48 centimeters/second to 609.6 centimeters/second, and wherein the flow of the degassed ionic liquid to the ATR window provides self-cleaning of the ATR window.

13. The process of claim 11, wherein the solvent is flowed over a face of the ATR window and particulates that have adhered to the ATR window are dissolved and washed away by the solvent, then the purging gas is separately flowed over the face of the ATR window and the purging dries the ATR window and lines that had previously conducted the solvent.

14. The process of claim 11, wherein a hydrolyzed ionic liquid, a corrosion product, or a mixture thereof, that had adhered to the ATR window, is dissolved and removed by the solvent.

15. The process of claim 11, wherein the solvent is an alcohol, a water, or a mixture thereof.

16. The process of claim 11, wherein the ionic liquid is a slipstream from a continuous operation of the process unit.

17. The process of claim 11, wherein the online FTIR instrument is located at the bottom of a hydrocarbon/ionic liquid separator and provides a calculated value for the chemical concentration within 10 minutes, enabling a rapid response to upsets in an operation of a hydrocarbon conversion unit using the ionic liquid.

18. The process of claim 11, additionally comprising validating a calibration of the online FTIR instrument using a validation ionic liquid with a known value of the chemical concentration during the periodically redirecting step c).

19. The process of claim 11, wherein the chemical concentration is related to an activity of the ionic liquid for performing a hydrocarbon conversion; and the process unit utilizing the ionic liquid performs the hydrocarbon conversion selected from the group consisting of an alkylation, a dimerization, an oligomerization, an acylation, a hydrocracking, a metathesis, a copolymerization, an isomerization, a carbonylation, a hydroformylation, a dehalogenation, a dehydration, a disproportionation, a transalkylation, and combinations thereof.

20. The process of claim 11, wherein a flash drum pressure during the degassing is from 0 to 100 psig, allowing isobutane to vaporize and be removed.

* * * * *